US009339536B2

(12) United States Patent
Chou et al.

(10) Patent No.: US 9,339,536 B2
(45) Date of Patent: May 17, 2016

(54) FUSION PROTEINS FOR USE AS IMMUNOGENIC ENHANCERS FOR INDUCING ANTIGEN-SPECIFIC T CELL RESPONSES

(71) Applicant: TheVax Genetics Vaccine Co., Ltd., Taipei (TW)

(72) Inventors: Wei-I Chou, Hsinchu County (TW); Chia-Mao Wu, Hsinchu County (TW); Jiun-Ming Wu, Hsinchu County (TW); Hsiu-Kang Chang, Taipei (TW)

(73) Assignee: TheVax Genetics Vaccine Co., Ltd., Taipei (TW)

( * ) Notice: Subject to any disclaimer, the term of this patent is extended or adjusted under 35 U.S.C. 154(b) by 273 days.

(21) Appl. No.: 14/095,947

(22) Filed: Dec. 3, 2013

(65) Prior Publication Data

US 2014/0154280 A1 Jun. 5, 2014

Related U.S. Application Data

(60) Provisional application No. 61/733,879, filed on Dec. 5, 2012.

(51) Int. Cl.

| | |
|---|---|
| ***C07K 14/21*** | (2006.01) |
| ***C07K 19/00*** | (2006.01) |
| ***A61K 39/02*** | (2006.01) |
| ***A61K 39/385*** | (2006.01) |
| ***A61K 39/21*** | (2006.01) |
| ***C07K 14/005*** | (2006.01) |
| ***A61K 47/48*** | (2006.01) |
| ***C07K 14/705*** | (2006.01) |
| *A61K 39/00* | (2006.01) |

(52) U.S. Cl.

CPC ............... *A61K 39/21* (2013.01); *A61K 39/385* (2013.01); *A61K 47/4833* (2013.01); *C07K 14/005* (2013.01); *C07K 14/70596* (2013.01); *A61K 2039/6031* (2013.01); *C07K 2319/02* (2013.01); *C07K 2319/04* (2013.01); *C07K 2319/095* (2013.01); *C07K 2319/33* (2013.01); *C07K 2319/40* (2013.01); *C12N 2710/20034* (2013.01); *C12N 2750/10034* (2013.01)

(58) Field of Classification Search

CPC ..................... C07K 2319/04; C07K 2319/095; C07K 2319/09; C07K 2319/01; C07K 2319/02; C07K 2319/10; A61K 2309/6031; A61K 39/385; A61K 47/4833; A61K 39/104; A61K 2039/6031

See application file for complete search history.

(56) References Cited

U.S. PATENT DOCUMENTS

| | | | | |
|---|---|---|---|---|
| 7,314,632 | B1 | 1/2008 | Fitzgerald | |
| 7,335,361 | B2 | 2/2008 | Liao et al. | |
| 7,378,100 | B2 | 5/2008 | Chang et al. | |
| 7,465,455 | B2 | 12/2008 | Chang et al. | |
| 2005/0119470 | A1 * | 6/2005 | Manoharan .... | C12Y 306/05002 536/22.1 |

OTHER PUBLICATIONS

Fukuda M et al. (1996) Cytoplasmic localization of mitogen-activated protein kinase kinase directed by its NH2-terminal, leucine-rich short amino acid sequence, which acts as a nuclear export signal. J. Biol. Chem. 271(33):20024-20028.*

Goletz TJ et al. Delivery of antigens to the MHC Class I pathway using bacterial toxins. Human Immunology, 1997, 54:129-136.*

Lippolis JD et al. (2000) Pseudomonas exotoxin-mediated delivery of exogenous antigens to MHC class I and class II processing pathways. Cell. Immunol. 203:75-83.*

Moron G et al. (2004) New tools for antigen delivery to the MHC class I pathway. Trends in Immunol. 25(2):92-97.*

Takemoto S et al. (2009) Enhanced generation of cytotoxic T lymphocytes by increased cytosolic delivery of MHC class I epitope fused to mouse heat shock protein 70 viw polyhistidine conjugation. J. Controlled Release, 135:11-18.*

D. Craig Hooper et al. "Rabies ribonucleocapsid as an oral immunogen and immunological enhancer" Proc. Natl. Acad. Sci. USA, vol. 91, pp. 10908-10912. Nov. 1994, Immunology.

Derek T O'Hagan;"New Generation Vaccine Adjuvants" Encyclopedia of Life Sciences & 2007. John Wiley & Sons, Ltd., pp. 1-7.

Theuer et al. "Domain ll of Pseudomonas Exotoxin A Arrests the Transfer of Translocating Nascent Chains into Mammalian Microsomes" Biochemistry 1994, 33, 5894-5900.

* cited by examiner

*Primary Examiner* — Kimberly A. Ballard

(74) *Attorney, Agent, or Firm* — Hsiu-Ming Saunders; Intellectual Property Connections, Inc.

(57) ABSTRACT

A vaccine composition comprising a fusion protein for inducing enhanced pathogen antigen-specific T cell responses is disclosed. The fusion protein comprises: (a) an antigen-presenting cell (APC)-binding domain or a CD91 receptor-binding domain, located at the N-terminus of the fusion protein; (b) a translocation peptide of 34-112 amino acid residues in length, comprising an amino acid sequence that is at least 90% identical to SEQ ID NO: 4, 2, 3, or 6, located at the C-terminus of the APC-binding domain or the CD91 receptor-binding domain; and (c) an antigen of a pathogen, located at the C-terminus of the translocation peptide; (d) a nuclear export signal, comprising the amino acid sequence of SEQ ID NO: 13; and (e) an endoplasmic reticulum retention sequence, located at the C-terminus of the fusion protein.

20 Claims, 2 Drawing Sheets

1. Placebo
2. $PE_{407}$-ORF2-K3
3. $PE_{313}$-ORF2-NESK

1. Placebo
2. $PE_{407}$-E2-K3
3. $PE_{313}$-E2-NESK

1. Placebo
2. $PE_{407}$-VP1-3A-K3
3. $PE_{313}$-VP1-3A-NESK

1. Placebo
2. $PE_{407}$-FHN-K3
3. $PE_{313}$-FHN-NESK

| Group | Antigen | Adjuvant | μg/dose |
|---|---|---|---|
| A | Placebo | AS04C | - |
| B | $PE_{407}$-E7-K3 | AS04C | 100 |
| C | RAP1-$PE_{268-313}$-E7-K3 | AS04C | 100 |
| C | RAP1-$PE_{268-313}$-E7-NESK | AS04C | 100 |

FUSION PROTEINS FOR USE AS IMMUNOGENIC ENHANCERS FOR INDUCING ANTIGEN-SPECIFIC T CELL RESPONSES

REFERENCE TO RELATED APPLICATION

The present application claims the priority to U.S. Provisional Application Ser. No. 61/733,879, filed Dec. 5, 2012, which is herein incorporated by reference in its entirety.

FIELD OF THE INVENTION

The present invention relates generally to fusion proteins and immunology.

BACKGROUND OF THE INVENTION

Molecular biology has enabled the production of subunit vaccines, in which the immunogen is a fragment or a subunit of a parent protein or complex. The development of a stable vaccine that could elicit T cell sensitizing responses, and be flexible enough to incorporate sequences from many strains of an infectious agent would be desirable.

SUMMARY OF THE INVENTION

In one aspect, the invention relates to a fusion protein comprising:

(a) an antigen-presenting cell (APC)-binding domain or a CD91 receptor-binding domain, located at the N-terminus of the fusion protein;

(b) a translocation peptide of 34-112 amino acid residues in length, comprising an amino acid sequence that is at least 90% identical to SEQ ID NO: 4, 2, 3, or 6, located at the C-terminus of the APC-binding domain or the CD91 receptor-binding domain; and (c) an antigen of a pathogen, located at the C-terminus of the translocation peptide;

(d) a nuclear export signal, comprising the amino acid sequence of SEQ ID NO: 13; and (e) an endoplasmic reticulum retention sequence, located at the C-terminus of the fusion protein.

In one embodiment of the invention, the APC-binding domain or the CD91 receptor-binding domain is a polypeptide comprising an amino acid sequence that is at least 90% identical to the sequence selected from the group consisting of SEQ ID NOs: 1 and 8-11.

In another embodiment of the invention, the nuclear export signal comprises the amino acid sequence of SEQ ID NO: 14.

In another embodiment of the invention, the endoplasmic reticulum retention sequence comprises the amino acid sequence of SEQ ID NO: 15.

In another embodiment of the invention, the nuclear export signal is located between the translocation peptide and the antigen.

In another embodiment of the invention, the nuclear export signal is located between the antigen and the endoplasmic reticulum retention sequence.

In another embodiment of the invention, the nuclear export signal and the ER retention sequence forms a fusion peptide comprising an amino acid sequence that is at least 90% identical to SEQ ID NO: 12.

In another embodiment of the invention, the translocation peptide has 34-61 amino acid residues in length.

In another embodiment of the invention, the translocation peptide has 34-46 amino acid residues in length.

In another embodiment of the invention, the APC-binding domain or the CD91 receptor-binding domain is free of the amino acid sequence of *Pseudomonas* exotoxin A (PE) binding domain I.

In another embodiment of the invention, the APC-binding domain or the CD91 receptor-binding domain comprises the amino acid sequence of SEQ ID NO: 8.

In another embodiment of the invention, the amino acid sequence of the APC-binding domain or the CD91 receptor-binding domain is SEQ ID NO: 1.

In another embodiment of the invention, the antigen is a fusion antigen of two or more antigenic peptides from a pathogen.

In another embodiment of the invention, the ER retention sequence has more than 4 amino acid residues in length.

In another embodiment of the invention, the translocation peptide comprises an amino acid sequence that is at least 95% identical to SEQ ID NO: 4, 2, 3, or 6.

In another embodiment of the invention, the APC-binding domain or the CD91 receptor-binding domain exhibits a characteristics of recognizing and binding to a receptor on an antigen-presenting cell (APC) selected from the group consisting of dendritic cells, monocytes. B-cells and lymphocytes.

In another embodiment of the invention, the pathogen is selected from the group consisting of PRRSV, PCV, FMDV, CSFV, NDV, Transmissible gastroenteritis virus (TGEV), Porcine epidemic diarrhea virus (PEDV), Influenza virus. Pseudorabies virus. Prvovirus, Pseudorabies virus, Swine vesicular disease virus (SVDV), Poxvirus, Rotavirus, *Mycoplasma* pneumonia, Herpes virus, Infectious bronchitis, and Infectious bursal disease virus.

In another aspect, the invention consists essentially of, or consisting of:

(a) an antigen-presenting cell (APC)-binding domain or a CD91 receptor-binding domain, located at the N-terminus of the fusion protein;

(b) a translocation peptide of 34-112 amino acid residues in length, comprising an amino acid sequence that is at least 90% identical to SEQ ID NO: 4, 2, 3, or 6, located at the C-terminus of the APC-binding domain or the CD91 receptor-binding domain; and (c) an antigen of a pathogen, located at the C-terminus of the translocation peptide;

(d) a nuclear export signal, comprising the amino acid sequence of SEQ ID NO: 13; and (e) an endoplasmic reticulum retention sequence, located at the C-terminus of the fusion protein.

Further in another aspect, the invention relates to a vaccine composition comprising the fusion protein as aforementioned and an adjuvant.

Yet in another aspect, the invention relates to a method for inducing enhanced pathogen antigen-specific T cell responses, comprising: administering a vaccine composition comprising a therapeutically effective amount of the fusion protein of the invention to a subject in need thereof, and thereby inducing enhanced pathogen antigen-specific T cell responses.

2A-5A) and CD4⁺/IFN-γ⁺ T cell (FIGS. 2B-5B) mediated immunogenicities, respectively.

Figure 6:
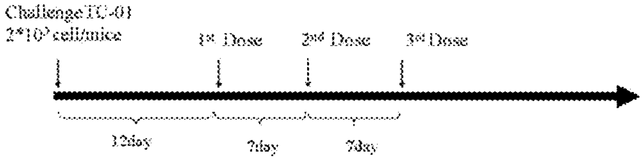

FIG. 6 shows animal groups, vaccines and dosage used for immunizing the animals, and immunization schedules.

Figure 7:
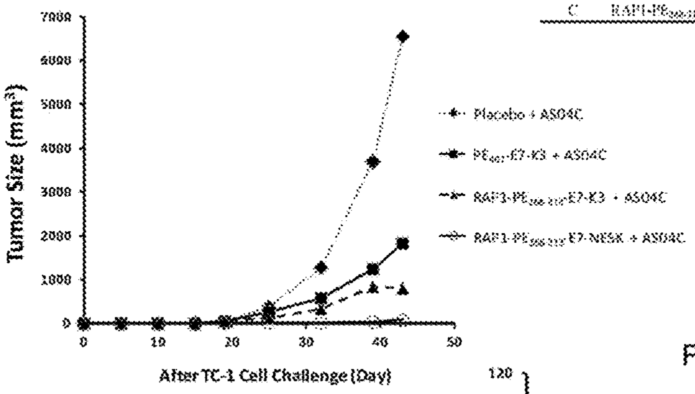
Figure 8:
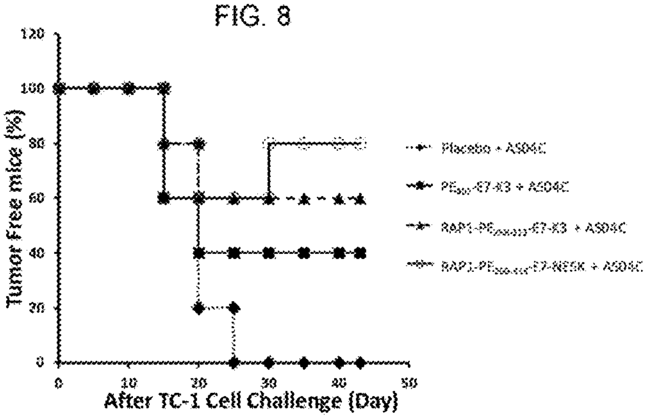

FIGS. 7-8 are graphs showing tumor size curves and percentage of tumor-free mice in the animal groups vaccinated with various fusion proteins or placebo, respectively.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "an antigen-presenting cell (APC) or accessory cell" refers to a cell that displays foreign antigens complexed with major histocompatibility complexes (MHC's) on their surfaces. T-cells may recognize these complexes using their T-cell receptors (TCRs). These cells process antigens and present them to T-cells. Main types of professional antigen-presenting cell are dendritic cells (DCs), macrophages, which are also CD4+ and are therefore also susceptible to infection by HIV; monocytes, and certain B-cells.

The term "an antigen-presenting cell (APC)-binding domain" refers to a domain (which is a polypeptide) that can bind to an antigen-presenting cell (APC). The APC-binding domain may be a polypeptide comprising an amino acid sequence that is at least 90% identical to the sequence selected from the group consisting of SEQ ID NOs: 1 and 8-11. An APC-binding domain is a ligand that recognizes and binds to a receptor on APC.

Cluster of differentiation 91 (CD91) is a protein that forms a receptor in the membrane of cells and is involved in receptor-mediated endocytosis.

The term "$PE_t$" refers to a translocation peptide (or a translocation domain) with 34-112 amino acid residues in length. $PE_t$ may comprises the amino acid sequence that is at least 90% identical to SEQ ID NO: 2-4 and 6. For example, the amino acid sequence of $PE_t$ may be a fragment of a.a. 280-a.a. 313 (SEQ ID NO: 4), a.a. 268-a.a. 313 (SEQ ID NO: 3), aa. 253-a.a. 313 (SEQ ID NO: 2), or a.a. 253-a.a. 364 (SEQ ID NO: 6) of PE. That is, the amino acid sequence of $PE_t$ may contain any region of the PE domain II (a.a. 253 to a.a. 364: SEQ ID NO: 6) as long as it comprises a.a 280-a.a. 313 (SEQ ID NO: 4) essential sequence (i.e., the essential fragment).

The $PE_{407}$ (SEQ ID NO: 7) is described in prior patent (U.S. Pat. No. 7,335,361 B2) as PE(ΔIII).

The term "minimum translocation peptide" refers to $PE_{253-313}$ (SEQ ID NO: 2), which can translocate an antigen into the cytoplasm of a target cell.

The term "an endoplasmic reticulum (ER) retention sequence" refers to a peptide whose function is to assist translocation of an antigen from the cytoplasm into ER and retains the antigen in the lumen of the ER. An ER retention sequence comprises the sequence of Lys Asp Glu Leu (KDEL; SEQ ID NO: 15) or RDEL. An ER retention sequence may comprise the sequence KDEL, RDEL, KDELKDELKDEL (K3; SEQ ID NO: 16), KKDL-RDELKDEL (K3; SEQ ID NO: 17), KKDELRDELKDEL (K3; SEQ ID NO: 18), or KKDELRVELKDEL (K3; SEQ ID NO: 19).

A nuclear export signal (NES) refers to a short amino acid sequence of 4 hydrophobic residues in a protein that targets it for export from the cell nucleus to the cytoplasm through the nuclear pore complex using nuclear transport. The NES is recognized and bound by exportins. The most common spacing of the hydrophobic residues to be $L_{xx}KL_{xx}L_xL_x$ (SEQ ID NO. 13), where "L" is leucine, "K" is lysine and "x" is any naturally occurring amino acid. For example, an artificial NES may comprise the sequence Leu Gln Lys Lys Leu Glu Glu Leu Glu Leu Ala (LQKKLEELELA; SEQ ID NO: 14).

The term "NESK" refers to a fusion peptide of a NES and an ER retention signal (i.e., a NES fused to an ER retention signal). It is an artificial peptide possessing the function of a nuclear export signal (NES) and an ER retention sequence. Thus, it can export an antigen from the cell nucleus to the cytoplasm through the nuclear pore complex, and assist translocation of an antigen from the cytoplasm to ER and retain the antigen in the lumen of the ER. For example, the amino acid sequence of NESK may be LQKKLEELELAKDEL (SEQ ID NO: 12).

An antigen may be a pathogenic protein, polypeptide or peptide that is responsible for a disease caused by the pathogen, or is capable of inducing an immunological response in a host infected by the pathogen, or tumor-associated antigen (TAA) which is a polypeptide specifically expressed in tumor cells. The antigen may be selected from a pathogen or cancer cells including, but not limited to, Human Papillomavirus (HPV), Porcine reproductive and respiratory syndrome virus (PRRSV), Human immunodeficiency virus-1 (HIV-1), Dangue virus, Hepatitis C virus (HCV), Hepatitis B virus (HBV), Porcine Circovirus 2 (PCV2), Classical Swine Fever Virus (CSFV), Foot-and-mouth disease virus (FMDV), Newcastle disease virus (NDV), Transmissible gastroenteritis virus (TGEV), Porcine epidemic diarrhea virus (PEDV), Influenza virus. Pseudorabies virus, Prvovirus, Pseudorabies virus, Swine vesicular disease virus (SVDV), Poxvirus, Rotavirus, *Mycoplasma pneumonia*, Herpes virus, infectious bronchitis, or infectious bursal disease virus, non-small cell lung cancer, breast carcinoma, melanoma, lymphomas, colon carcinoma, hepatocellular carcinoma and any combination thereof. For example, HPV E7 protein (E7), HCV core protein (HCV core), HBV X protein (HBx) were selected as antigens for vaccine development. The antigen may be a fusion antigen from a fusion of two or more antigens selected from one or more pathogenic proteins. For example, a fusion antigen of PRRSV ORF6 and ORF5 fragments, or a fusion of antigenic proteins from PRRSV and PCV2 pathogens.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The invention relates to fusion proteins for enhancing antigen delivery and modulating cell-mediated immune response. The fusion protein comprises: (a) an antigen-presenting cell (APC)-binding domain or a CD91 receptor-binding domain, located at the N-terminus of the fusion protein; (b) a translocation peptide of 34-112 amino acid residues in length, comprising an amino acid sequence that is at least 90% identical to SEQ ID NO: 2-4 and 6 and located at the C-terminus of the APC-binding domain or the CD91 receptor-binding domain; and (c) an antigen of a pathogen, located at the C-terminus of the translocation peptide; (d) a nuclear export signal (NES); and (e) an endoplasmic reticulum (ER) retention sequence, the ER retention sequence being located at the C-terminus of the fusion protein, wherein the NES comprises the amino acid sequence of SEQ ID NO: 13.

Using the fusion protein $PE_{313}$-ORF2-NESK as an example, the strategy is that the fusion protein of the invention stimulates the production and activation of T cells that can recognize the antigen Porcine Circovirus Type 2 (PCV2) capsid protein ORF2. The fusion protein comprises, from N-terminus to C-terminus, a PE domain I (APC-binding domain), a translocation peptide of 34-112 amino acid residues in length (e.g., a.a. 253-313 of the PE domain 11), a truncated PCV2 ORF2 protein (N-terminal nuclear localization signal removed), a NES signal and an ER retention sequence (KDEL). The underlying mechanisms of eliciting enhanced ORF2-specific T cell immune responses by $PE_{313}$-ORF2-NESK involve the following steps: a) binding to dendritic cell (or antigen-presenting cell) surface receptor (CD91); b) internalization by endocytosis; c) transporting to the ER and proteolytic hydrolysis by furin in front of the translocation peptide; d) processing and presenting by MHC 1 complex; and e) activating antigen-specific CD4+ and CD8+ T cells. CD4+ Th1 cells are able to efficiently stimulate and enhance cytotoxic CD8+ T cell immune response. Together, these two arms of the adaptive immune system have the specificity and potency to kill PCV2 and PCV2-infected cells.

The fusion protein $PE_{313}$-ORF2-NESK here is distinguishable from the fusion protein vaccine $PE_{407}$-Ag-K3 disclosed by Lai in U.S. Pat. No. 7,335,361 in several aspects. Firstly, the length of $PE_{313}$ (SEQ ID NO: 5) is 94 amino acid residues shorter than $PE_{407}$ (SEQ ID NO: 7), the advantage of which is that unwanted humoral response elicited by the presence of an extra fragment of PE is minimized or eliminated. Secondly, the ER retention sequence is shortened. Instead of K3 (that is, 3 of KDER), only one KDER or RDER is needed. Thirdly, only cytosolic antigen can be processed and presented by MHC type 1 pathway, so the addition of a NES signal into the fusion protein is beneficial to enhance pathogen antigen-specific T cell responses because increasing the opportunity of translocation of antigen into cytosol. Antigens of a pathogen may be imported into the cell nucleus. By incorporating a NES signal, the antigen imported into the cell nucleus can be exported to the cytoplasm by the NES signal of the fusion protein.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein however, in no way they, whether they are right or wrong, should limit the scope of the invention so long as the invention is practiced according to the invention without regard for any particular theory or scheme of action.

Example 1

Construction of Expression Vectors

Figure 1A:
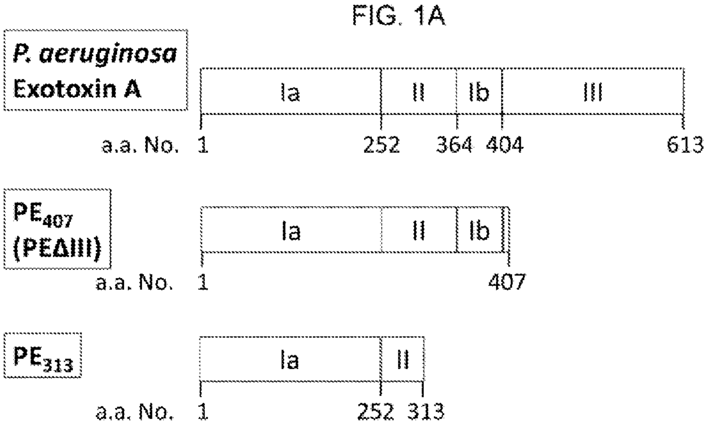
FIG. 1A is a schematic drawing showing a full-length *Pseudomonas aeruginosa* exotoxin A (PE), and partial fragment of PE.

FIG. 1A shows PE contains 3 domains (I, II, and III). $PE_{407}$ is the region from aa. 1 to a.a407 of PE. $PE_{407}$ does not contain the cytotoxic domain III and thus contains domains I and II. $PE_{313}$ the region from as 1 to a.a. 313 of PE. Thus, $PE_{313}$ contains only domain Ia and a partial N-terminal region of domain II of PE.

Figure 1B:
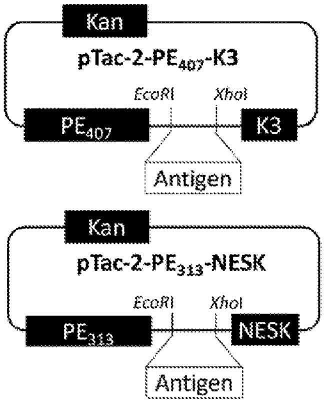
FIGS. 1B-C show vector maps.
Figure 1C:
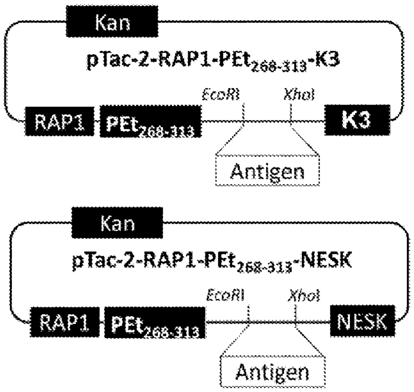

FIGS. 1B-C show constructions of expression vectors, each of which comprises an antigen-presenting cell (APC)-binding domain, a translocation peptide, an antigen, with (bottom panel) or without (top panel) a nuclear export signal (NES); and an endoplasmic reticulum (ER) retention sequence (top panel, K3 or bottom panel, K), the ER retention sequence being located at the C-terminus of the fusion protein. The plasmids pTac-2-$PE_{313}$-NESK, pTac-2-$PE_{407}$-K3, pTac-2-RAP1-$PE_{268-313}$-NESK and pTac-2-RAP1-$PE_{268-313}$-K3 were generated as follows: The $^{NdeI}PE_{313}$-$^{(EcoRI,\ XhoI)}$-NESK$^{XhoI}$, $^{NdeI}PE_{407}$-$^{(EcoRI,\ XhoI)}$-K3$^{XhoI}$, $^{NdeI}$RAP1-$^{(EcoRI)}$-$PE_{268-313}$-$^{(EcoRI,\ XhoI)}$-NESK$^{XhoI}$ and $^{NdeI}$RAP1-$^{(EcoRI)}$-$PE_{268-313}$-$^{(EcoRI,\ XhoI)}$-K3$^{XhoI}$ fragments were synthesized by a PCR method and then ligated into a pUC18 back bond with kanamycin resistance gene to obtain respective plasmids.

A target DNA encoding an antigen or a fusion antigen of a pathogen of interest may then be inserted into the aforementioned plasmids to generate an expression vector for expression of a fusion protein. For example, DNA fragments encoding antigens of Porcine Circovirus Type 2 (PCV2) ORF2

(SEQ ID NO: 20), Classical Swine Fever Virus (CSFV) E2 (SEQ ID NO: 21). Foot-and-mouth disease virus (FMDV) VP1-3A (SEQ ID NO: 24) and Newcastle disease virus (NDV) FHN (SEQ ID NO: 27) were synthesized and inserted into the plasmids pTac-2-$PE_{313}$-NESK and pTac-2-$PE_{407}$-K3, respectively, to generate the following expression vectors: (1) $PE_{313}$-ORF2-NESK; (2) $PE_{407}$-ORF2-K3; (3) $PE_{313}$-E2-NESK; (4) $PE_{407}$-E2-K3; (5) $PE_{313}$-VP1-3A-NESK; (6) $PE_{407}$-VP1-3A- K3; (7) $PE_{313}$-FHN-NESK; and (8) $PE_{407}$-FHN-K3. DNA fragments encoding antigen of Human Papillomavirus Type 16 E7 (SEQ ID NO: 28) were synthesized and inserted into the plasmids pTac-2-$PE_{407}$-K3, pTac-2-RAP1-$PE_{268-313}$-NESK and pTac-2-RAP1-$PE_{268-313}$-K3, respectively, to generate the following expression vectors: (9) $PE_{407}$-E7-K3, (10) RAP1-$PE_{268-313}$-E7-NESK and (11) RAP1-$PE_{268-313}$-E7-K3.

Example 2

Protein Expression

*E. coli* BL21 cells harboring plasmids for expression of fusion proteins (1) $PE_{313}$-ORF2-NESK; (2) $PE_{407}$-ORF2-K3; (3) $PE_{313}$-E2-NESK; (4) $PE_{407}$-E2-K3; (5) $PE_{313}$-VP1-3A-NESK; (6) $PE_{407}$-VP1-3A-K3; (7) $PE_{313}$-FHN-NESK; (8) $PE_{407}$-FHN-K3; (9) $PE_{407}$-K3; (10) RAP1-$PE_{268-313}$-E7-NESK and (11) RAP1-$PE_{268-313}$-E7-K3 were respectively cultured in Luria Bertani broth containing 25 ppm of kanamycin at 37° C. When the culture reaching early log phase, (A600=0.1 to 0.4), isopropyl-1-thio-β-D-galactopyranoside (IPTG) was added with a final concentration of 0.5 to 2 mM for induction. Cells were harvested after induction after 4 hours and immediately stored at −70° C. The fusion proteins were purified by urea extraction as described previously (Liao et al., 1995. Appl. Microbiol. Biotechnol. 43: 498-507) and then were refolded by dialysis method against 50× volume of TNE buffer (50 mM Tris, 50 mM NaCl and 1 mM EDTA) at 4° C. for overnight. The refolded proteins were subjected to SDS-PAGE analyses and quantitative analyses performed using Bradford Protein Assay Kit (Pierce). The results indicated that most of the refolded proteins were monomers under a non-reduced condition, indicating that the fusion proteins refolded easily and were not aggregated.

Example 3

PCV2 Subunit Vaccines Immunogenicity Assay

Mice were vaccinated with 0.1 ml PCV2 subunit vaccine containing 40 μg of $PE_{313}$-ORF2-NESK or $PE_{407}$-ORF2-K3 with aluminum phosphate (a protein absorbent for slow release of the fusion protein; 10% v/v) and 10 g of saponin (an adjuvant extracted from *Quillaja saponaria*) via s.c. injection once a week for 3 weeks. The control group (placebo) was injected with adjuvant only without the fusion protein. All mice were sacrificed 14 days after the last immunization, and the spleens were harvested. The splenocytes were isolated and cultured in 6-well plate ($10^8$ cells/2 ml/well) with or without the recombinant ORF2 protein in the presence of 1 μg/ml GolgiPlug (BD Pharmingen, San Diego, Calif.) at 37° C. for 16 hr. The stimulated splenocytes were then washed with FACScan buffer and stained with phycoerythrin-conjugated monoclonal rat anti-mouse CD8a and AF700-conjugated monoclonal rat anti-mouse CD4 antibodies. Cells were intracellular cytokine stained using the Cytofix/Cytoperm kit according to the manufacturer's instructions (BD Pharmingen). Intracellular IFN-γ was stained with AF488-conjugated rat anti-mouse IFN-γ to measure the immune response and cytokine levels. Flow cytometry analyses were performed using Gallios flow cytometry with Kaluza analysis software (Beckman Coulter).

Figure 2A:
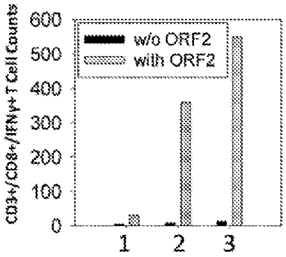
FIGS. 2-5 are graphs showing fusion proteins according to the invention eliciting enhanced $CD8^+$/IFN-$\gamma^+$ T cell (FIGS.
Figure 2B:
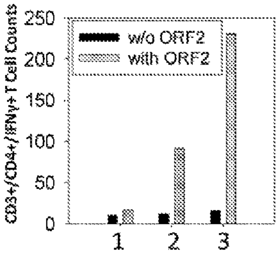

FIGS. 2A-B show the numbers of CD8 and CD4 positive IFN-γ T cells in the splenocytes from mice vaccinated with a placebo (adjuvant only without the fusion protein) or fusion proteins, respectively. The IFN-γ production by CD4+ and CD8+ T cells in splenocytes stimulated with ORF2 was detected by intracelluar staining via flow cytometry. Bar graphs show the numbers of ORF2-specific IFN-γ+ CD4+ T cells (FIG. 2B) and IFN-γ+ CD8+ T cells (FIG. 2A) from each group with (grey bars) or without (black bars) stimulation by the ORF2 peptide. The results indicated that the mice that had been vaccinated with $PE_{313}$-ORF2-NESK had more ORF2-specific CD4+ IFN-γ and CD8+ IFN-γ+T cells stimulated by the ORF2 peptide than the mice that had been vaccinated with $PE_{407}$-ORF2-K3 group.

Example 4

CSFV Subunit Vaccines Immunogenicity Assay

Using the same immunization schedule and dosage, mice were vaccinated with CSFV subunit vaccines containing $PE_{313}$-E2-NESK or $PE_{407}$-E2-K3, and splenocytes isolated, cultured and assayed by a flow cytometry method as described above, except that the recombinant E2 protein was added to stimulate the splenocytes in the culture.

Figure 3A:
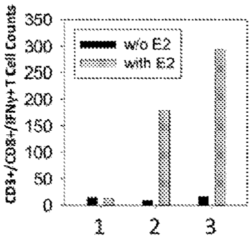
Figure 3B:
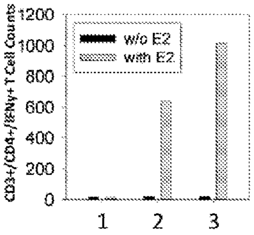

FIGS. 3A-B show the numbers of CD8 and CD4 positive IFN-γ T cells in the splenocytes from mice vaccinated with a placebo (adjuvant only without the fusion protein) or fusion proteins, respectively. The IFN-γ production by CD4+ and CD8+ T cells in splenocytes stimulated with E2 was detected by intracelluar staining via flow cytometry. Bar graphs show the numbers of E2-specific IFN-γ+ CD4+ T cells (FIG. 3B) and IFN-γ+ CD8+ T cells (FIG. 3A) from each group with (grey bars) or without (black bars) stimulation by the E2 peptide. The results indicated that the mice that had been vaccinated with $PE_{313}$-E2-NESK had more E2-specific CD4+ IFN-γ+ and CD8+ IFN-γ+ T cells stimulated by the E2 peptide than the mice that had been vaccinated with $PE_{407}$-E2-K3 group.

Example 5

FMDV Subunit Vaccines Immunogenicity Assay

Using the same immunization schedule and dosage, mice were vaccinated with FMDV subunit vaccines containing $PE_{313}$-VP1-3A-NESK or $PE_{407}$-VP1-3A-K3, and splenocytes isolated, cultured and assayed by a flow cytometry method as described above, except that the recombinant VP1-3A protein was added to stimulate the splenocytes in the culture.

Figure 4A:
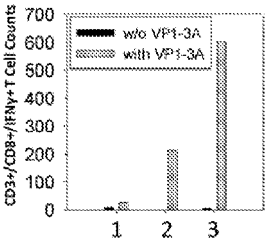
Figure 4B:
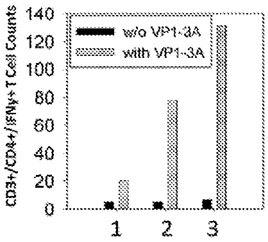

FIGS. 4A-B show the numbers of CD8 and CD4 positive IFN-γ T cells in the splenocytes from mice vaccinated with a placebo or fusion proteins. The IFN-γ production by CD4+ and CD8+ T cells in splenocytes stimulated with VP1-3A was detected by intracelluar staining via flow cytometry. Bar graphs show the numbers of VP1-3A-specific IFN-γ+ CD4+ T cells (FIG. 4B) and IFN-γ+ CD8+ T cells (FIG. 4A) from each group with (grey bars) or without (black bars) stimulation t the VP1-3A peptide. The results indicated that the mice that had been vaccinated with $PE_{313}$-VP1-3A-NESK had more VP1-3A-specific CD4+ IFN-γ+ and CD8+ IFN-γ+ T cells stimulated by the VP1-3A peptide than the mice that had been vaccinated with $PE_{407}$VP1-3A-K3 group.

Example 6

NDV Subunit Vaccines Immunogenicity Assay

Using the same immunization schedule and dosage, mice were vaccinated with FMDV subunit vaccines containing $PE_{313}$-FHN-NESK or $PE_{407}$-FHN-K3, and splenocytes isolated, cultured and assayed by a flow cytometry method as described above, except that the recombinant FHN protein was added to stimulate the splenocytes in the culture.

Figure 5A:
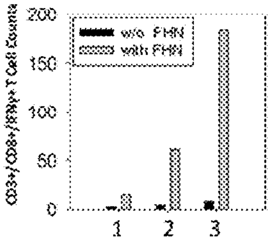
Figure 5B:
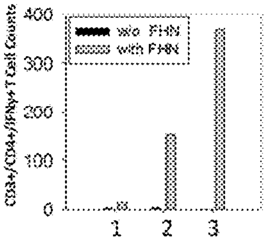

FIGS. 5A-B show the numbers of CD8 and CD4 positive IFN-γ T cells in the splenocytes from mice vaccinated with a placebo or fusion proteins. The IFN-γ production by CD4+ and CD8+ T cells in splenocytes stimulated with FHN was detected by intracelluar staining via flow cytometry. Bar graphs show the numbers of FHN-specific IFN-γ+ CD4+ T cells (FIG. 5B) and IFN-γ+ CD8+ T cells (FIG. 5A) from each group with (grey bars) or without (black bars) stimulation by the FHN peptide. The results indicated that the mice that had been vaccinated with $PE_{313}$-FHN-NESK had more FHN specific CD4+ IFN-γ+ and CD8+ IFN-γ+ T cells stimulated by the FHN peptide than the mice that had been vaccinated with $PE_{407}$-FHN-K3 group.

Example 7

Enhanced Inhibition of Tumor Growth Induced by Human Papilloma Virus Type 16 E7 Protein The fusion proteins $PE_{407}$-E7-K3, RAP1-$PE_{268-313}$-E7-K3 and RAP1-$PE_{268-313}$-E7-NESK were expressed and refolded using similar methods as described above. Mice were challenged with $2\times10^3$ TC-01 cells (mouse lung epithelia cell harboring HPV type 16 E7 gene) via s.c. injection to induce HPV-16 type carcinoma. Twelve days after the TC-01 cell challenge, mice were vaccinated via s.c. with placebo (PBS), $PF_{407}$-E7-K3 (100 mg/dose), RAP1-$PE_{268-313}$-E7-K3 (100 μg/dose) or RAP1-$PE_{268-313}$-E7-NESK (100 μg/dose) with AS04C (GlaxoSmithKline) as an adjuvant once per week for 3 weeks (FIG. 6). AS04C, which is a cytotoxic T lymphocyte-enhancing adjuvant, comprises MPL (monophosphoryl lipid A, an immune potentiator) and aluminum phosphate (a protein absorbent for antigen deliver). The term "K3" refers to an ER retention sequence comprising KDEL. For example, K3 may be the amino acid sequence KDELKDELKDEL (SEQ ID NO: 16). The term "NESK" refers to a fusion peptide comprising a nuclear export signal and an ER retention sequence. In one embodiment of the invention, the NESK is the amino acid sequence LQKKLEELELAKDEL (SEQ ID NO: 12). The size of tumors and the number of tumor-free animals in each group were recorded (FIGS. 7 and 8). The tumor growth was significantly suppressed by vaccines $PE_{407}$-K3, RAP1-$PE_{268-313}$-E7-K3 and RAP1-$PE_{268-313}$-E7-NESK with AS04C as an adjuvant. However, the vaccine RAP1-$PE_{268-313}$-E7-NESK was superior to $PE_{407}$-E7-K3 and better than RAP1-$PE_{268-313}$-E7-K3 in suppressing tumor growth and increasing the percentage of tumor-free animals.

Example 8

The following fusion proteins are generated $PE_{313}$-NES-antigen-K, $PE_{1-252}$-$PE_{268-313}$-NES-antigen-K, $PE_{1-252}$-$PE_{280-313}$-NES-antigen-K. In addition, the fragment of PE domain Ia ($PE_{1-252}$) of the fusion protein $PE_{313}$-antigen-NESK is replaced by RAP1 domain 3 (SEQ ID NO: 8). A2M minimum (SEQ ID NO: 9), HIV-Tat minimum (SEQ ID NO: 10) or HSPs minimum (SEQ ID NO: 11) to generate the fusion proteins RAP1 domain 3-$PE_{253-313}$-antigen-NESK, A2M-$PE_{253-313}$-antigen-NESK, Tat-$PE_{253-313}$-antigen-NESK and HSP-$PE_{253-313}$-antigen-NESK, RAP1 domain 3-$PE_{268-313}$-antigen-NESK, A2M-$PE_{268-313}$-antigen-NESK, Tat-$PE_{268-313}$-antigen-NESK and HSP-$PE_{268-313}$-antigen-NESK vaccines, RAP1 domain 3-$PE_{280-313}$-antigen-NESK, A2M-$PE_{280-313}$-antigen-NESK, Tat-$PE_{280-313}$-antigen-NESK and HSP-$PE_{280-313}$-antigen-NESK, respectively. RAP1 domain 3-$PE_{253-313}$-NES-antigen-K, A2M-$PE_{253-313}$-NES-antigen-K, Tat-$PE_{253-313}$-NES-antigen-K and HSP-$PE_{253-313}$-NES-antigen-K, RAP1 domain 3-$PE_{268-313}$-NES-antigen-K. A2M-$PE_{268-313}$-NES-antigen-K, Tat-$PE_{268-313}$-NES-antigen-K and HSP-$PE_{268-313}$-NES-antigen-K vaccines, RAP1 domain 3-$PE_{280-313}$-NES-antigen-K. A2M-$PE_{280-313}$-NES-antigen-K, Tat-$PE_{280-313}$-NES-antigen-K and HSP-$PE_{280-313}$-NES-antigen-K. The cell mediated immune responses enhanced by these vaccines are examined using similar methods as described above.

Table 1 shows SEQ ID NOs. of peptides used for making various fusion proteins.

TABLE 1

| Component | SEQ ID NO: | amino acid residues |
|---|---|---|
| Minimum *Pseudomonas* exotoxin A (PE) binding domain Ia (APC-binding domain, a.a.1-a.a.252 of PE) | 1 | 252 |
| $PE_{253-313}$ | 2 | 61 |
| $PE_{268-313}$(translocation domain) | 3 | 46 |
| $PE_t$ Core (PE translocation domain core; a.a. 280-a.a. 313 of PE) | 4 | 34 |
| $PE_{313}$ (a.a. 1-a.a. 313 of PE) | 5 | 313 |
| $PF_{253-364}$ | 6 | 112 |
| $PE_{407}$ aa. 1-a.a. 407 of PE) | 7 | 407 |
| RAP1 Minimum (domain III of RAP1) | 8 | 104 |
| A2M Minimum | 9 | 153 |
| HIV-Tat Minimum | 10 | 24 |

TABLE 1 -continued

| Component | SEQ ID NO: | amino acid residues |
|---|---|---|
| HSPs Minimum | 11 | 641 |
| NESK is **LQKKLEELELA**<u>KDEL</u>* | 12 | 15 |
| NES consensus sequence is $L_{XX}KL_{XX}L_{X}L_{X}$, wherein "L" is leucine, "K" is lysine and "$_X$" is any naturally occurring amino acid. | 13 | 11 |
| NES is LQKKLEELELA | 14 | 11 |
| KDEL | 15 | 4 |
| KDELKDELKDEL (K3) | 16 | 12 |
| KKDERDELKDEL (K3) | 17 | 12 |
| KKDELRDELKDEL (K3) | 18 | 13 |
| KKDELRVELKDEL (K3) | 19 | 13 |
| PCV2 ORF2 (*Porcine Circovirus type 2* Open Reading Frame 2) | 20 | 192 |
| CSFV E2 (*Classical Swine Fever Virus* Envelope glycoprotein E2) | 21 | 328 |
| FMDV VP1 peptide (viral capsid protein a.a. 127-a.a. 176 of VP1) | 22 | 50 |
| FMDV 3A peptide (a.a. 21-35 of 3A) | 23 | 15 |
| FMDV (Foot-and-Mouth Disease Virus) VP1-3A peptide** | 24 | 65 |
| NDV F peptide (a.a. 65-a.a. 82 of Fusion protein) | 25 | 18 |
| NDV HN peptide (a.a. 101-a.a. 111 of Hemagglutinin-Neuraminidase) | 26 | 11 |
| NDV FHN peptide*** | 27 | 29 |
| HPV (Human *Papillomavirus*) Type16 E7 | 28 | 98 |
| Full length PE (Exotoxin A. *Pseudomonas aeruginosa*) | 29 | 613 |

*The bold letters represents the amino acid sequence of an artificial nuclear exporting signal, the underlined letters represents the amino acid sequence of an endoplasmic reticulum retention signal.
**The VP1-3A peptide is a fusion antigen composed of a.a. 127-aa. 176 of VP1 and a.a. 21-a.a. 35 of 3A: i.e., a fusion of FMDV VP1 peptide (SEQ ID NO: 22. and FMDV 3A peptide (SEQ ID NO 23).
***The FHN peptide is a fusion antigen composed of a.a. 65-a.a. 82 of fusion protein and (a.a. 101 aa. 111 of Hemagglutinin-Neuraminidase, i.e, a fusion of NDV F peptide (SEQ ID NO: 25) and NDV HN peptide (SEQ ID NO: 26)

In summary, the results have proved that a fusion protein containing an APC-binding domain at the N-terminal end, a translocation domain, followed by an antigen of a pathogen, and then a fusion peptide of NESK at the carboxyl terminal end is an improved design over the PE-fusion protein that is without the fusion peptide of NESK at the carboxyl terminus in terms of enhancing cell-mediated immune response, suppressing tumor growth, and/or increasing the percentage of tumor-free animals.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A fusion protein comprising;

(a) an antigen-presenting cell (APC)-binding domain or a CD91 receptor-binding domain, located at the N-terminus of the fusion protein;

(b) a translocation peptide of 34-112 amino acid residues in length, comprising an amino acid sequence that is at least 90% identical to SEQ ID NO: 4, 2, or 3, located at the C-terminus of the APC-binding domain or the CD91 receptor-binding domain; and (c) an antigen of a pathogen;

(d) a nuclear export signal, comprising the amino acid sequence of SEQ ID NO: 13, wherein the C-terminal amino acid of the SEQ ID NO: 13 is alanine; and (e) an endoplasmic reticulum retention sequence, located at the C-terminus of the fusion protein;

wherein the nuclear export signal is located between the antigen and the endoplasmic reticulum retention sequence, or between the translocation peptide and the antigen.

2. The fusion protein of claim 1, wherein the APC-binding domain or the CD91 receptor-binding domain is a polypeptide comprising an amino acid sequence that is at least 90% identical to the sequence selected from the group consisting of SEQ ID NOs: 1 and 8-11.

3. The fusion protein of claim 1, wherein the nuclear export signal comprises the amino acid sequence of SEQ ID NO: 14.

4. The fusion protein of claim 1, wherein the endoplasmic reticulum retention sequence comprises the amino acid sequence of SEQ ID NO: 15.

5. The fusion protein of claim 1, wherein the nuclear export signal is located between the translocation peptide and the antigen.

6. The fusion protein of claim 1, wherein the nuclear export signal is located between the antigen and the endoplasmic reticulum retention sequence.

7. The fusion protein of claim 1, wherein the nuclear export signal and the ER retention sequence forms a fusion peptide comprising an amino acid sequence that is at least 90% identical to SEQ ID NO: 12.

8. The fusion protein of claim 1, wherein the translocation peptide has 34-61 amino acid residues in length.

9. The fusion protein of claim 1, wherein the APC-binding domain or the CD91 receptor-binding domain is free of the amino acid sequence of *Pseudomonas* exotoxin A (PE) binding domain I.

10. The fusion protein of claim 9, wherein the APC-binding domain or the CD91 receptor-binding domain comprises the amino acid sequence of SEQ ID NO: 8.

11. The fusion protein of claim 1, wherein the amino acid sequence of the APC-binding domain or the CD91 receptor-binding domain is SEQ ID NO: 1.

12. The fusion protein of claim 11, wherein the translocation peptide has 34-61 amino acid residues in length.

13. The fusion protein of claim 12, wherein the nuclear export signal and the ER retention sequence forms a fusion peptide with an amino acid sequence that is at least 90% identical to SEQ ID NO: 12.

14. The fusion protein of claim 11, wherein the translocation peptide has 34-46 amino acid residues in length.

15. The fusion protein of claim 10, wherein the translocation peptide has 34-61 amino acid residues in length.

16. The fusion protein of claim 15, wherein the nuclear export signal and the ER retention sequence forms a fusion peptide with an amino acid sequence that is at least 90% identical to SEQ ID NO: 12.

17. The fusion protein of claim 1, wherein the antigen is a fusion antigen of two or more antigenic peptides from a pathogen.

18. A fusion protein comprising:

(a) an antigen-presenting cell (APC)-binding domain or a CD91 receptor-binding domain, located at the N-terminus of the fusion protein;

(b) a translocation peptide of 34-61 amino acid residues in length, comprising an amino acid sequence that is at least 90% identical to SEQ ID NO: 4, 2, 3, or 6, located at the C-terminus of the APC-binding domain or the CD91 receptor-binding domain; and (c) an antigen of a pathogen;

(d) a nuclear export signal, comprising the amino acid sequence of SEQ ID NO: 13; and (e) an endoplasmic reticulum retention sequence, located at the C-terminus of the fusion protein;

wherein the nuclear export signal is located between the antigen and the endoplasmic reticulum retention sequence, or between the translocation peptide and the antigen.

19. A vaccine composition comprising the fusion protein of claim 1 and an adjuvant.

20. A method for inducing enhanced pathogen antigen-specific T cell responses, comprising:

administering a vaccine composition comprising a therapeutically effective amount of the fusion protein of claim 1 to a subject in need thereof, and thereby inducing enhanced pathogen antigen-specific T cell responses.

* * * * *

SEQUENCE LISTING

<160> NUMBER OF SEQ ID NOS: 29

<210> SEQ ID NO 1
<211> LENGTH: 252
<212> TYPE: PRT
<213> ORGANISM: Pseudomonas aeruginosa

<400> SEQUENCE: 1

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu
                245                 250
```

<210> SEQ ID NO 2
<211> LENGTH: 61
<212> TYPE: PRT
<213> ORGANISM: Pseudomonas aeruginosa

<400> SEQUENCE: 2

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg
    50                  55                  60
```

-continued

<210> SEQ ID NO 3
<211> LENGTH: 46
<212> TYPE: PRT
<213> ORGANISM: Pseudomonas aeruginosa

<400> SEQUENCE: 3

Pro Leu Glu Thr Phe Thr Arg His Arg Gln Pro Arg Gly Trp Glu Gln
1 5 10 15

Leu Glu Gln Cys Gly Tyr Pro Val Gln Arg Leu Val Ala Leu Tyr Leu
20 25 30

Ala Ala Arg Leu Ser Trp Asn Gln Val Asp Gln Val Ile Arg
35 40 45

<210> SEQ ID NO 4
<211> LENGTH: 34
<212> TYPE: PRT
<213> ORGANISM: Pseudomonas aeruginosa

<400> SEQUENCE: 4

Gly Trp Glu Gln Leu Glu Gln Cys Gly Tyr Pro Val Gln Arg Leu Val
1 5 10 15

Ala Leu Tyr Leu Ala Ala Arg Leu Ser Trp Asn Gln Val Asp Gln Val
20 25 30

Ile Arg

<210> SEQ ID NO 5
<211> LENGTH: 313
<212> TYPE: PRT
<213> ORGANISM: Pseudomonas aeruginosa

<400> SEQUENCE: 5

Ala Glu Glu Ala Phe Asp Leu Trp Asn Glu Cys Ala Lys Ala Cys Val
1 5 10 15

Leu Asp Leu Lys Asp Gly Val Arg Ser Ser Arg Met Ser Val Asp Pro
20 25 30

Ala Ile Ala Asp Thr Asn Gly Gln Gly Val Leu His Tyr Ser Met Val
35 40 45

Leu Glu Gly Gly Asn Asp Ala Leu Lys Leu Ala Ile Asp Asn Ala Leu
50 55 60

Ser Ile Thr Ser Asp Gly Leu Thr Ile Arg Leu Glu Gly Gly Val Glu
65 70 75 80

Pro Asn Lys Pro Val Arg Tyr Ser Tyr Thr Arg Gln Ala Arg Gly Ser
85 90 95

Trp Ser Leu Asn Trp Leu Val Pro Ile Gly His Glu Lys Pro Ser Asn
100 105 110

Ile Lys Val Phe Ile His Glu Leu Asn Ala Gly Asn Gln Leu Ser His
115 120 125

Met Ser Pro Ile Tyr Thr Ile Glu Met Gly Asp Glu Leu Leu Ala Lys
130 135 140

Leu Ala Arg Asp Ala Thr Phe Phe Val Arg Ala His Glu Ser Asn Glu
145 150 155 160

Met Gln Pro Thr Leu Ala Ile Ser His Ala Gly Val Ser Val Val Met
165 170 175

Ala Gln Thr Gln Pro Arg Arg Glu Lys Arg Trp Ser Glu Trp Ala Ser
180 185 190

Gly Lys Val Leu Cys Leu Leu Asp Pro Leu Asp Gly Val Tyr Asn Tyr
195 200 205

-continued

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg
305                 310

<210> SEQ ID NO 6
<211> LENGTH: 112
<212> TYPE: PRT
<213> ORGANISM: Pseudomonas aeruginosa

<400> SEQUENCE: 6

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110

<210> SEQ ID NO 7
<211> LENGTH: 407
<212> TYPE: PRT
<213> ORGANISM: Pseudomonas aeruginosa

<400> SEQUENCE: 7

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

```
Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val
                405


<210> SEQ ID NO 8
<211> LENGTH: 104
<212> TYPE: PRT
<213> ORGANISM: Homo sapiens

<400> SEQUENCE: 8

Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
            20                  25                  30

Lys His Phe Glu Ala Lys Ile Glu Lys His Asn His Tyr Gln Lys Gln
        35                  40                  45

Leu Glu Ile Ala His Glu Lys Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80
```

-continued

Arg Thr Lys Glu Leu Gly Tyr Thr Val Lys Lys His Leu Gln Asp Leu
85 90 95

Ser Gly Arg Ile Ser Arg Ala Arg
100

<210> SEQ ID NO 9
<211> LENGTH: 153
<212> TYPE: PRT
<213> ORGANISM: Artificial Sequence
<220> FEATURE:
<223> OTHER INFORMATION: A2M Minimum

<400> SEQUENCE: 9

Val Tyr Leu Gln Thr Ser Leu Lys Tyr Asn Ile Leu Pro Glu Lys Glu
1 5 10 15

Glu Phe Pro Phe Ala Leu Gly Val Gln Thr Leu Pro Gln Thr Cys Asp
20 25 30

Glu Pro Lys Ala His Thr Ser Phe Gln Ile Ser Leu Ser Val Ser Tyr
35 40 45

Thr Gly Ser Arg Ser Ala Ser Asn Met Ala Ile Val Asp Val Lys Met
50 55 60

Val Ser Gly Phe Ile Pro Leu Lys Pro Thr Val Lys Met Leu Glu Arg
65 70 75 80

Ser Asn His Val Ser Arg Thr Glu Val Ser Ser Asn His Val Leu Ile
85 90 95

Tyr Leu Asp Lys Val Ser Asn Gln Thr Leu Ser Leu Phe Phe Thr Val
100 105 110

Leu Gln Asp Val Pro Val Arg Asp Leu Lys Pro Ala Ile Val Lys Val
115 120 125

Tyr Asp Tyr Tyr Glu Thr Asp Glu Phe Ala Ile Ala Glu Tyr Asn Ala
130 135 140

Pro Cys Ser Lys Asp Leu Gly Asn Ala
145 150

<210> SEQ ID NO 10
<211> LENGTH: 24
<212> TYPE: PRT
<213> ORGANISM: Artificial Sequence
<220> FEATURE:
<223> OTHER INFORMATION: HIV-Tat Minimum

<400> SEQUENCE: 10

Arg Gly Asp Pro Thr Gly Gln Glu Glu Ser Lys Glu Lys Val Glu Lys
1 5 10 15

Glu Thr Val Val Asp Pro Val Thr
20

<210> SEQ ID NO 11
<211> LENGTH: 641
<212> TYPE: PRT
<213> ORGANISM: Artificial Sequence
<220> FEATURE:
<223> OTHER INFORMATION: HSPs Minimum

<400> SEQUENCE: 11

Met Ala Lys Ala Ala Ala Ile Gly Ile Asp Leu Gly Thr Thr Tyr Ser
1 5 10 15

Cys Val Gly Val Phe Gln His Gly Lys Val Glu Ile Ile Ala Asn Asp
20 25 30

-continued

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

-continued

```
Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp


<210> SEQ ID NO 12
<211> LENGTH: 15
<212> TYPE: PRT
<213> ORGANISM: Artificial Sequence
<220> FEATURE:
<223> OTHER INFORMATION: NESK

<400> SEQUENCE: 12

Leu Gln Lys Lys Leu Glu Glu Leu Glu Leu Ala Lys Asp Glu Leu
1               5                   10                  15


<210> SEQ ID NO 13
<211> LENGTH: 11
<212> TYPE: PRT
<213> ORGANISM: Artificial Sequence
<220> FEATURE:
<223> OTHER INFORMATION: NES consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Leu Xaa Xaa Lys Leu Xaa Xaa Leu Xaa Leu Xaa
1               5                   10
```

-continued

<210> SEQ ID NO 14
<211> LENGTH: 11
<212> TYPE: PRT
<213> ORGANISM: Artificial Sequence
<220> FEATURE:
<223> OTHER INFORMATION: NES

<400> SEQUENCE: 14

Leu Gln Lys Lys Leu Glu Glu Leu Glu Leu Ala
1 5 10

<210> SEQ ID NO 15
<211> LENGTH: 4
<212> TYPE: PRT
<213> ORGANISM: Artificial Sequence
<220> FEATURE:
<223> OTHER INFORMATION: ER retention sequence

<400> SEQUENCE: 15

Lys Asp Glu Leu
1

<210> SEQ ID NO 16
<211> LENGTH: 12
<212> TYPE: PRT
<213> ORGANISM: Artificial Sequence
<220> FEATURE:
<223> OTHER INFORMATION: K3

<400> SEQUENCE: 16

Lys Asp Glu Leu Lys Asp Glu Leu Lys Asp Glu Leu
1 5 10

<210> SEQ ID NO 17
<211> LENGTH: 12
<212> TYPE: PRT
<213> ORGANISM: Artificial Sequence
<220> FEATURE:
<223> OTHER INFORMATION: K3

<400> SEQUENCE: 17

Lys Lys Asp Leu Arg Asp Glu Leu Lys Asp Glu Leu
1 5 10

<210> SEQ ID NO 18
<211> LENGTH: 13
<212> TYPE: PRT
<213> ORGANISM: Artificial Sequence
<220> FEATURE:
<223> OTHER INFORMATION: K3

<400> SEQUENCE: 18

Lys Lys Asp Glu Leu Arg Asp Glu Leu Lys Asp Glu Leu
1 5 10

<210> SEQ ID NO 19
<211> LENGTH: 13
<212> TYPE: PRT
<213> ORGANISM: Artificial Sequence
<220> FEATURE:
<223> OTHER INFORMATION: K3

<400> SEQUENCE: 19

Lys Lys Asp Glu Leu Arg Val Glu Leu Lys Asp Glu Leu
1 5 10

-continued

<210> SEQ ID NO 20
<211> LENGTH: 192
<212> TYPE: PRT
<213> ORGANISM: Artificial Sequence
<220> FEATURE:
<223> OTHER INFORMATION: truncated PCV2 ORF2

<400> SEQUENCE: 20

```
Asn Gly Ile Phe Asn Thr Arg Leu Ser Arg Thr Phe Gly Tyr Thr Ile
1               5                   10                  15

Lys Arg Thr Thr Val Lys Thr Pro Ser Trp Ala Val Asp Met Met Arg
            20                  25                  30

Phe Asn Ile Asn Asp Phe Leu Pro Pro Gly Gly Gly Ser Asn Pro Arg
        35                  40                  45

Ser Val Pro Phe Glu Tyr Tyr Ser Ile Ser Lys Val Lys Val Glu Phe
    50                  55                  60

Trp Pro Cys Ser Pro Ile Thr Gln Gly Asp Ser Gly Val Gly Ser Ser
65                  70                  75                  80

Ala Val Ile Leu Asp Asp Asn Phe Val Thr Lys Ala Thr Ala Leu Thr
                85                  90                  95

Tyr Asp Pro Tyr Val Asn Tyr Ser Ser Arg His Thr Ile Thr Gln Pro
            100                 105                 110

Phe Ser Tyr His Ser Arg Tyr Phe Thr Pro Lys Pro Val Leu Asp Ser
        115                 120                 125

Thr Ile Asp Tyr Phe Gln Pro Asn Asn Lys Arg Asn Gln Leu Trp Leu
    130                 135                 140

Arg Leu Gln Thr Ala Gly Asn Val Asp His Val Gly Leu Gly Thr Ala
145                 150                 155                 160

Phe Glu Asn Ser Ile Tyr Asp Gln Glu Tyr Asn Ile Arg Val Thr Met
                165                 170                 175

Tyr Val Gln Phe Arg Glu Phe Asn Leu Lys Asp Pro Pro Leu Asn Pro
            180                 185                 190
```

<210> SEQ ID NO 21
<211> LENGTH: 328
<212> TYPE: PRT
<213> ORGANISM: Artificial Sequence
<220> FEATURE:
<223> OTHER INFORMATION: truncated CSFV E2

<400> SEQUENCE: 21

```
Arg Leu Ser Cys Lys Glu Asp His Arg Tyr Ala Ile Ser Ser Thr Asn
1               5                   10                  15

Glu Ile Gly Pro Leu Gly Ala Glu Gly Leu Thr Thr Thr Trp Lys Glu
            20                  25                  30

Tyr Ser His Gly Leu Gln Leu Asp Asp Gly Thr Val Arg Ala Ile Cys
        35                  40                  45

Ile Ala Gly Ser Phe Lys Val Thr Ala Leu Asn Val Val Ser Arg Arg
    50                  55                  60

Tyr Leu Ala Ser Leu His Lys Arg Ala Leu Pro Thr Ser Val Thr Phe
65                  70                  75                  80

Glu Leu Leu Phe Asp Gly Thr Ser Pro Ala Ile Glu Glu Met Gly Glu
                85                  90                  95

Asp Phe Gly Phe Gly Leu Cys Pro Phe Asp Thr Thr Pro Val Val Lys
            100                 105                 110

Gly Lys Tyr Asn Thr Thr Leu Leu Asn Gly Ser Ala Phe Tyr Leu Val
        115                 120                 125
```

Cys Pro Ile Gly Trp Thr Gly Val Ile Glu Cys Thr Ala Val Ser Pro
130 135 140

Thr Thr Leu Arg Thr Glu Val Val Lys Thr Phe Lys Arg Glu Lys Pro
145 150 155 160

Phe Pro His Arg Ala Asp Cys Val Thr Thr Ile Val Glu Lys Glu Asp
165 170 175

Leu Phe His Cys Lys Leu Gly Gly Asn Trp Thr Cys Val Lys Gly Asn
180 185 190

Pro Val Thr Tyr Thr Gly Gly Gln Val Lys Gln Cys Arg Trp Cys Gly
195 200 205

Phe Asp Phe Lys Glu Pro Asp Gly Leu Pro His Tyr Pro Ile Gly Lys
210 215 220

Cys Ile Leu Ala Asn Glu Thr Gly Tyr Arg Val Val Asp Ser Thr Asp
225 230 235 240

Cys Asn Arg Asp Gly Val Val Ile Ser Thr Glu Gly Glu His Glu Cys
245 250 255

Leu Ile Gly Asn Thr Thr Val Lys Val His Ala Leu Asp Gly Arg Leu
260 265 270

Ala Pro Met Pro Cys Arg Pro Lys Glu Ile Val Ser Ser Ala Gly Pro
275 280 285

Val Arg Lys Thr Ser Cys Thr Phe Asn Tyr Thr Lys Thr Leu Arg Asn
290 295 300

Lys Tyr Tyr Glu Pro Arg Asp Ser Tyr Phe Gln Gln Tyr Met Leu Lys
305 310 315 320

Gly Glu Tyr Gln Tyr Trp Phe Asp
325

<210> SEQ ID NO 22
<211> LENGTH: 50
<212> TYPE: PRT
<213> ORGANISM: Artificial Sequence
<220> FEATURE:
<223> OTHER INFORMATION: FMDV VP1 peptide

<400> SEQUENCE: 22

Ala Thr Val Tyr Asn Gly Ser Ser Lys Tyr Gly Asp Thr Ser Thr Ser
1 5 10 15

Asn Val Arg Gly Asp Leu Gln Val Leu Ala Gln Lys Ala Glu Arg Thr
20 25 30

Leu Pro Thr Ser Phe Asn Phe Gly Ala Ile Lys Ala Thr Arg Val Thr
35 40 45

Glu Leu
50

<210> SEQ ID NO 23
<211> LENGTH: 15
<212> TYPE: PRT
<213> ORGANISM: Artificial Sequence
<220> FEATURE:
<223> OTHER INFORMATION: FMDV 3A peptide

<400> SEQUENCE: 23

Ala Ala Ile Glu Phe Phe Glu Gly Met Val His Asp Ser Ile Lys
1 5 10 15

<210> SEQ ID NO 24
<211> LENGTH: 65
<212> TYPE: PRT
<213> ORGANISM: Artificial Sequence -continued
<220> FEATURE:
<223> OTHER INFORMATION: FMDV VP1-3A peptide

<400> SEQUENCE: 24

Ala Thr Val Tyr Asn Gly Ser Ser Lys Tyr Gly Asp Thr Ser Thr Ser
1 5 10 15

Asn Val Arg Gly Asp Leu Gln Val Leu Ala Gln Lys Ala Glu Arg Thr
20 25 30

Leu Pro Thr Ser Phe Asn Phe Gly Ala Ile Lys Ala Thr Arg Val Thr
35 40 45

Glu Leu Ala Ala Ile Glu Phe Phe Glu Gly Met Val His Asp Ser Ile
50 55 60

Lys
65

<210> SEQ ID NO 25
<211> LENGTH: 18
<212> TYPE: PRT
<213> ORGANISM: Artificial Sequence
<220> FEATURE:
<223> OTHER INFORMATION: NDV F peptide

<400> SEQUENCE: 25

Leu Leu Pro Asn Met Pro Lys Asp Lys Glu Gly Cys Ala Lys Ala Pro
1 5 10 15

Leu Glu

<210> SEQ ID NO 26
<211> LENGTH: 11
<212> TYPE: PRT
<213> ORGANISM: Artificial Sequence
<220> FEATURE:
<223> OTHER INFORMATION: NDV HN peptide

<400> SEQUENCE: 26

Pro Asp Glu Gln Asp Tyr Gln Ile Arg Met Ala
1 5 10

<210> SEQ ID NO 27
<211> LENGTH: 29
<212> TYPE: PRT
<213> ORGANISM: Artificial Sequence
<220> FEATURE:
<223> OTHER INFORMATION: NDV FHN peptide

<400> SEQUENCE: 27

Leu Leu Pro Asn Met Pro Lys Asp Lys Glu Gly Cys Ala Lys Ala Pro
1 5 10 15

Leu Glu Pro Asp Glu Gln Asp Tyr Gln Ile Arg Met Ala
20 25

<210> SEQ ID NO 28
<211> LENGTH: 98
<212> TYPE: PRT
<213> ORGANISM: Human papillomavirus type 16

<400> SEQUENCE: 28

Met His Gly Asp Thr Pro Thr Leu His Glu Tyr Met Leu Asp Leu Gln
1 5 10 15

Pro Glu Thr Thr Asp Leu Tyr Cys Tyr Glu Gln Leu Asn Asp Ser Ser
20 25 30

-continued

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln
85 90 95

Lys Pro

<210> SEQ ID NO 29
<211> LENGTH: 613
<212> TYPE: PRT
<213> ORGANISM: Pseudomonas aeruginosa

<400> SEQUENCE: 29

Ala Glu Glu Ala Phe Asp Leu Trp Asn Glu Cys Ala Lys Ala Cys Val
1 5 10 15

Leu Asp Leu Lys Asp Gly Val Arg Ser Ser Arg Met Ser Val Asp Pro
20 25 30

Ala Ile Ala Asp Thr Asn Gly Gln Gly Val Leu His Tyr Ser Met Val
35 40 45

Leu Glu Gly Gly Asn Asp Ala Leu Lys Leu Ala Ile Asp Asn Ala Leu
50 55 60

Ser Ile Thr Ser Asp Gly Leu Thr Ile Arg Leu Glu Gly Gly Val Glu
65 70 75 80

Pro Asn Lys Pro Val Arg Tyr Ser Tyr Thr Arg Gln Ala Arg Gly Ser
85 90 95

Trp Ser Leu Asn Trp Leu Val Pro Ile Gly His Glu Lys Pro Ser Asn
100 105 110

Ile Lys Val Phe Ile His Glu Leu Asn Ala Gly Asn Gln Leu Ser His
115 120 125

Met Ser Pro Ile Tyr Thr Ile Glu Met Gly Asp Glu Leu Leu Ala Lys
130 135 140

Leu Ala Arg Asp Ala Thr Phe Phe Val Arg Ala His Glu Ser Asn Glu
145 150 155 160

Met Gln Pro Thr Leu Ala Ile Ser His Ala Gly Val Ser Val Val Met
165 170 175

Ala Gln Thr Gln Pro Arg Arg Glu Lys Arg Trp Ser Glu Trp Ala Ser
180 185 190

Gly Lys Val Leu Cys Leu Leu Asp Pro Leu Asp Gly Val Tyr Asn Tyr
195 200 205

Leu Ala Gln Gln Arg Cys Asn Leu Asp Asp Thr Trp Glu Gly Lys Ile
210 215 220

Tyr Arg Val Leu Ala Gly Asn Pro Ala Lys His Asp Leu Asp Ile Lys
225 230 235 240

Pro Thr Val Ile Ser His Arg Leu His Phe Pro Glu Gly Gly Ser Leu
245 250 255

Ala Ala Leu Thr Ala His Gln Ala Cys His Leu Pro Leu Glu Thr Phe
260 265 270

Thr Arg His Arg Gln Pro Arg Gly Trp Glu Gln Leu Glu Gln Cys Gly
275 280 285

Tyr Pro Val Gln Arg Leu Val Ala Leu Tyr Leu Ala Ala Arg Leu Ser
290 295 300

-continued

```
Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610
```